United States Patent [19]
Schaedlich et al.

[11] Patent Number: 5,660,795
[45] Date of Patent: Aug. 26, 1997

[54] CARTRIDGE FOR COLLECTION OF A SAMPLE BY ADSORPTION ONTO A SOLID SURFACE

[75] Inventors: Frank H. Schaedlich, Toronto; Daniel R. Schneeberger, Scarborough, both of Canada

[73] Assignee: Tekran Inc., Toronto, Canada

[21] Appl. No.: 388,924

[22] Filed: Feb. 16, 1995

Related U.S. Application Data

[63] Continuation-in-part of Ser. No. 201,949, Feb. 25, 1994, Pat. No. 5,597,535.
[51] Int. Cl.$^6$ .................................................. G01N 1/40
[52] U.S. Cl. ........................... 422/88; 422/91; 422/116; 436/81
[58] Field of Search ........................ 422/88, 91, 93, 422/116, 119, 211, 311; 73/1 G; 436/81

[56] References Cited

U.S. PATENT DOCUMENTS

| | | |
|---|---|---|
| 3,434,826 | 3/1969 | Holzmann . |
| 3,884,639 | 5/1975 | Sugiyama . |
| 4,023,929 | 5/1977 | Becker et al. . |
| 4,151,739 | 5/1979 | Breuer et al. . |
| 4,531,398 | 7/1985 | Di Benedetto et al. . |
| 5,026,652 | 6/1991 | Huber . |
| 5,384,101 | 1/1995 | Rockenfeller . |

*Primary Examiner*—Lyle A. Alexander
*Attorney, Agent, or Firm*—Bereskin & Parr

[57] ABSTRACT

A cartridge for collecting a sample of mercury or other substance of interest has a tubular housing and an insert, for example, of gold or another metal. The insert comprises a number of wire meshes sintered together to form a substantially unitary insert having an extended surface area, or otherwise is formed as a solid with a large surface area. The housing is provided with a groove and an internal projection as a mechanical coupling formations, to engage and retain the insert.

14 Claims, 1 Drawing Sheet

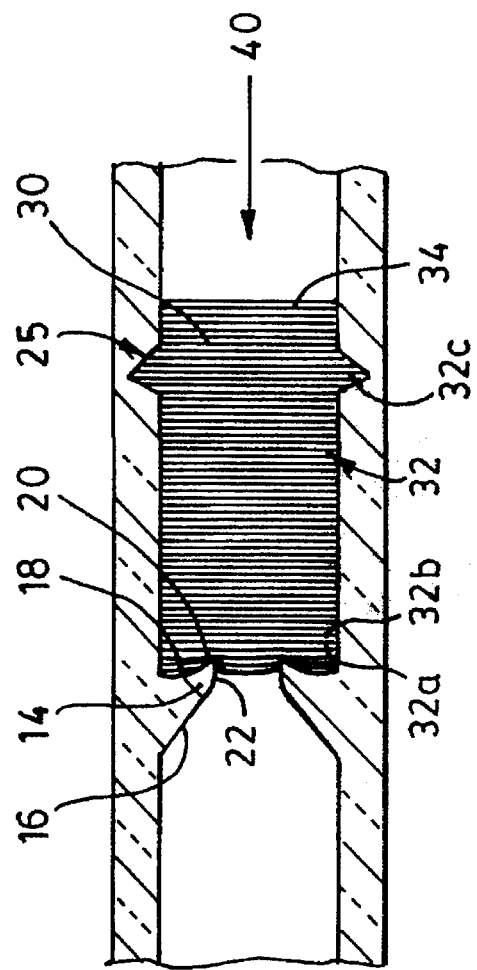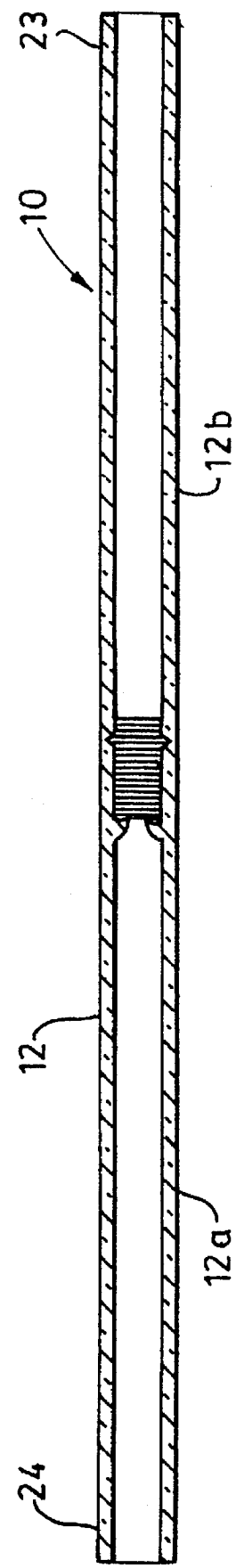

CARTRIDGE FOR COLLECTION OF A SAMPLE BY ADSORPTION ONTO A SOLID SURFACE

REFERENCE TO RELATED APPLICATION

This application is a Continuation-in-Part of our earlier application Ser. No. 08/201,949 filed Feb. 25, 1994, now U.S. Pat. No. 5,597,535, the contents of which are hereby incorporated by reference.

FIELD OF THE INVENTION

This invention relates to a cartridge for collection of a sample by adsorption of a substance or analyte of interest onto a solid surface. This invention more particularly, but not exclusively, relates to a cartridge for adsorbing mercury, for use in mercury detection apparatus. This invention more particularly relates to a cartridge including gold, adapted to adsorb mercury by forming an amalgam therewith.

BACKGROUND OF THE INVENTION

Mercury is an extremely toxic element. Numerous studies in North America and Europe have highlighted the problems of high mercury levels in food samples and the like, as well as the difficulties in the preservation of samples and the accurate and precise analysis of these.

Due to the toxic nature of mercury, even low levels can be significant. Accordingly, it is becoming increasingly desirable to measure mercury, in the amounts of parts per billion or parts per trillion, in air, water and food samples. Various techniques are known for detecting the presence of mercury. Two common techniques rely either on atomic absorption or atomic fluorescence. For atomic fluorescence, a Cold Vapour Atomic Fluorescence Spectrophotometer (CVAFS) is preferred. As compared to atomic absorption, the phenomenon is linear over a much wider range and is not subject to positive interferences.

Whatever technique is used, there is the fundamental problem of gathering a mercury sample. One well-known technique is to preconcentrate the mercury onto an adsorber. Here, it is well known that gold is an excellent adsorber for mercury, since the gold and mercury form an amalgam. Further, gold shows good properties, in terms of rejecting and not adsorbing possible contaminants, and the adsorbed mercury can be readily desorbed, simply by heating the gold. In this specification including the claims reference is made to "adsorption", which for the adsorption of mercury onto the surface of gold refers to the amalgamation of the mercury in a thin surface layer of the gold, so that there is no "absorption" into the interior of the gold. For other substances, in the specification including the claims, reference to "adsorption" is a reference to any process whereby a substance of interest is retained on the surface of a solid or in a thin surface layer immediately adjacent the surface, so as to be capable of being readily desorbed into a vapour steam.

However, when collecting minute or trace amounts of mercury, and to ensure an accurate measurement, it is necessary that the gold be in a form to provide a large surface area. Additionally, the configuration of the gold should be such as to provide an unimpeded passage for the relevant fluid through it.

One known technique relies upon the use of so-called Gold Sand. An article entitled "Monitoring Elemental Mercury in an Urban Environment" by P. B. Stockwell et al (Process Control and Quality, 1 (1991) 293–296) refers to the use of gold quartz sand to collect mercury, and makes reference to an article by R. Dumarey et al. The coated gold sand comprises quartz sand coated with a thin layer of gold. The sand is provided in a tube secured in place using quartz wool plugs. The problem with this arrangement is that the sand cracks or the gold layer flakes off, exposing chemically active sites that adsorb many interfering compounds. Microscopic sand and gold particles resulting from the breakdown can adsorb mercury and/or cause contamination of the downstream components. The quartz wool plugs cause problems since they adsorb a wide range of compounds other than mercury and release them into the detector in the heating cycle, causing erroneous results. Fine grain quartz wool will trap water under high humidity condensing conditions, which can cause numerous unwanted chemical processes to occur. Unlike quartz tubes, quartz wool presents a large number of active sites which can trap interfering compounds. This effect is particularly noticeable in cases where the ambient air contains common pollutants (e.g. $H_2S$, $SO_2$, $NO_x$), especially under high humidity conditions.

Some other known cartridges use gold coated glass beads rather than sand. These exhibit similar problems with the gold flaking and quartz wool end plugs, although the beads do not crack.

Other disclosures of the use of gold as an adsorbent can be found in U.S. Pat. Nos. 3,884,639; 4,023,929; 5,026,652.

The Sugiyama U.S. Pat. No. 3,884,639, discloses a mercury capturing zone including an amalgamating agent. It simply notes that the mercury or other amalgamating agent is a metal, such as gold, and that the metal may be used alone or may be carried on a heat-resistant support such as quartz powder.

The Becker et al U.S. Pat. No. 4,023,929 discloses a process for determining traces of mercury in liquids. An adsorption zone includes a gold wire mesh, but it gives no further detail of the structure of the wire mesh.

The Huber U.S. Pat. No. 5,026,652 discloses a method and device for mercury analysis. It simply mentions that it has a gold net for capturing the mercury.

It is to be appreciated that none of these patents discusses the detail of the mercury adsorption section of the device in any detail.

There are also numerous other fields where it is necessary to collect or preconcentrate an analyte or substance entrained in a fluid by either adsorption onto a solid surface. Two problems are almost always present, namely, (i) providing a large surface area, while maintaining a relatively low flow restriction; and (ii) maintaining an effective seal, so that a fluid cannot flow around the solid material. Feature (i) is desirable so that a large quantity of fluid can be passed through quickly to give a large sample; while feature (ii) is particularly relevant where heating and cooling cycles are used since inevitably the solid and a surrounding container have different coefficients of thermal expansion, and commonly heating is used to desorb a sample.

SUMMARY OF THE PRESENT INVENTION

What is required is a cartridge, including a solid, for adsorption of a sample of a substance or an analyte, which securely retains the solid, and provides the solid with as large a surface area as possible for the adsorption of the analyte. Preferably, the cartridge should not need to rely on other materials to support the solid, which may be a possible site for adsorption and subsequent desorption of contaminants. Further, the configuration of the solid should be such as to ensure that fluid flows over the solid surface, and that fluid is not permitted to flow around or bypass the solid, preventing capture of any substance or analyte of interest present.

In accordance with the present invention, there is provided a cartridge for collection of a sample of a substance or an analyte, the cartridge comprising: a housing having an inlet and an outlet and defining a bore for a fluid flow; and an insert of a solid capable of adsorbing said substance, which insert is substantially unitary, has a surface area for contact with fluid which is substantially larger than the surface area of an external profile of the insert, and extends across the bore to cause fluid to flow through the insert, wherein the housing includes a first coupling formation integrally formed with the housing from the material of the housing and the insert includes a second coupling formation integrally formed with the insert from the material of the insert, wherein one of the first or second coupling formations comprises an annular projection and the other one thereof comprises a complementary annular abutment surface which mechanically engage one another to retain the insert in position for flow in one direction and which are dimensioned to provide a convoluted path to reduce flow of fluid around the insert.

Preferably, the solid insert comprises a metal, a metal alloy or a compound of a metal such as gold, silver, platinum or iridium. For use in the detection of mercury a solid insert, in accordance with the present invention, comprises gold, whereby mercury is adsorbed onto the surface of the gold to form an amalgam. The material of the inset should have a higher affinity for the analyte or substance of interest, while preferably showing an ability to reject common contaminants.

Preferably, the housing is substantially tubular, and includes an internal annular projection, defining an orifice for fluid flow and engaging the insert. The housing preferably includes an internal retaining groove, and the insert includes a portion projecting into that retaining groove to retain the insert, the retaining groove being provided between the inlet and the annular projection.

In a preferred embodiment, the insert comprises a plurality of wire meshes sintered together and extending generally perpendicularly to the axis of the housing. The wire meshes are preferably formed from pure metal, a metal alloy, or a metal compound which is sinterable and can comprise, for example, gold. The wire meshes can comprise first meshes having a first mesh size and second meshes having a second, different mesh size, with the first and second meshes alternating with one another within the metal insert.

Where the housing includes an internal retaining groove, the wire meshes can comprise a first group of meshes which are circular and have the same diameter, corresponding to the diameter of the housing, and a second group of meshes which are circular, which are of larger diameter than the first group and which extend into the retaining groove.

In a second embodiment of the present invention there is provided a cartridge for the collection of a sample of a substance, the cartridge comprising: a housing having an inlet and an outlet and defining a bore for flow of fluid; and an insert capable of adsorbing substance of interest, which insert is substantially unitary, has a surface area for contact with fluid which is substantially larger than surface area of an external profile of the insert, and extends across the bore to cause fluid to flow through the insert, wherein the housing includes a internal annular projection integrally formed with the housing from the material of the housing and defining an orifice for fluid flow and mechanical engaging one end of the insert, to locate the insert and to provide a convoluted path to reduce fluid flow around the insert, and at the other end of the insert, the housing includes a retaining groove and the insert includes a portion integrally formed with the insert from material of the insert and projecting radially outwardly to engage the retaining groove and to provide a further convoluted path to reduce the fluid flow around the insert.

As in the first embodiment, for detection of mercury, the insert should comprise a plurality of wire meshes of gold. Also, these can be of alternating sizes and the insert can be secured by similar mechanical coupling formations.

BRIEF DESCRIPTION OF THE DRAWING FIGURES

For a better understanding of the present invention and to show more clearly how it may be carried into effect, reference will now be made, by way of example, to the accompanying drawings in which:

FIG. 1 is a sectional view through a cartridge in accordance with the present invention; and FIG. 2 is an enlarged sectional view of part of the cartridge of FIG. 1.

DESCRIPTION OF PREFERRED EMBODIMENT

As shown in the drawings, a cartridge 10 in accordance with the present invention has a housing comprising a tube of high purity quartz glass 12. This tube comprises first and second tube parts 12a and 12b.

One tube part is provided with an internal annular projection 14, which is shown as a generally conical face 16 on one side and a concave annular face 18 on the other side. It accordingly defines a circular projection 20, and a circular orifice 22.

Gas or other fluid is intended to flow from an inlet 23 to an outlet 24. Upstream from the orifice 22, i.e. closer to the inlet 23, relative to the usual direction of gas flow as detailed below, there is an annular retaining groove 25, which in section has a generally triangular profile, as shown. The groove may alternatively be rectangular in section Within the tube 12 retained by the retaining groove 25 and the projection 20, there is a sintered metal insert 30, whose assembly is detailed below. In this embodiment, the insert is formed from gold, although other materials can be used for detecting other substances or analytes. For fabrication purposes, the tube 12 comprises first and second tube parts 12a and 12b. These are joined at the orifice 22. The tube is formed in two parts simply because this is the easiest way to grind the groove 25 in the wall and to form the orifice 22. In this implementation, the groove 25 is formed by grinding, so that its profile will be determined by the shape of the tool used.

After the two parts 12a, 12b of the tube have been constructed and fused into a single assembly, the quartz tube is thoroughly cleaned of all impurities using heat, organic solvents and nitric acid.

Then, the gold insert 30 is assembled from a number of discs of woven gold wire. The discs are 99.995% pure gold. The basic dimensions of the insert 30 are an external diameter of 4 mm, and a length of 10 mm. The internal diameter of the tube 12 is also 4 mm and it has an outer diameter of 6 mm. It will be appreciated that other dimensions can be used, depending upon the application. In particular, it is desirable to reduce the size of the insert to the greatest extent possible so as to minimize the volume within the cartridge.

The insert is formed from a plurality of mesh discs, which are pressed together and then sintered, so that they fuse to form a unitary insert. Here, two different mesh sizes were used, namely, a 100×100 wires per inch gold weave and 52×52 wires per square gold weave (the designation 100× 100 indicates that the gold wires are woven in a rectangular grid with there being 100 wires per inch in each direction). The effective open area or cross section of the two mesh sizes is very similar, since the finer mesh is formed from 2.5 thousandths of an inch diameter wire and the larger mesh from 4 thousandths of an inch diameter wire.

The discs are indicated at 32 with the 100×100 wire weave being indicated at 32a and the 52×52 wires per inch gold weave indicated at 32b. The discs are stacked into the tube 12 alternating with one another. A hand tool is used to press each disc against the previously inserted discs. Stacking using alternating mesh sizes continues until the stack of discs protrudes just beyond the upstream edge (i.e. the right hand edge as viewed in the figures) of the retaining groove 25. The discs and tube assembly are then heated to approximately 600° C. This causes the discs to fuse together.

After cooling, the entire insert is compressed using a hand tool. This compresses the insert further to a point at the downstream (i.e. left hand as viewed in the figures) edge of the groove 25. A second batch of discs is then loaded into the cartridge using the same procedure and the same hand tool as described above. There are two differences, namely, slightly large discs 32c are used at the groove 25 so that the discs extend into the groove 25 and mechanically engage the groove 25, and the last ten discs inserted are all 100×100 weave. The number of alternating discs comprises approximately 100, there being 50 of each mesh size alternating with one another. When all the discs have been inserted, a second heating or sintering step is effected, again at 600° C. to sinter to all the discs together. Both the sintering steps are carried out in an inert atmosphere. After the second and final sintering step, and after cooling, the insert is again compressed using a hand tool.

The number of discs at each sintering step and in the final insert depends on the exact spacing between the orifice and the retaining groove. Pressure is applied to the hand tool after each disc has been inserted, and after each heating step.

In use, this configuration provides numerous advantages. The configuration of the retaining groove 25 and the projection 20 provides a secured dual seal arrangement. This is necessary to prevent an air or other sample from ducting around the perimeter of the gold insert. The seal arrangement forces air to pass through the interior of the insert, maximizing mercury adsorption.

The circular projection 20 of the annular lip 14 serves as a seat for the gold discs. The discs 32a, 32b nearest the orifice have been pressed into the shape of the projection 20 by heat and pressure applied during manufacture, as detailed above. Subsequent heating cycles during use cause the gold discs to further conform to the exact shape of the seat, providing a leak-tight seal. Then, should any sample air find a boundary passage between the insert and the inside of the tube 12, it is, at least at some point, forced into the interior of the insert 30, before exiting through the orifice 22.

Retaining groove 25 provides a second seal which serves two distinct functions. Firstly, it anchors the entire slug 30 in place so that it cannot move. Secondly, it acts as a flow diverter.

Sample gas flows in the direction 40, first contacts the upstream of the insert 30, i.e. the discs 34. Some of the air will flow through the matrix, but the majority would attempt to flow between the outer layer of the insert 30 and the inner surface of the quartz tube 12, this being the path of least resistance. However, this gas flow encounters the retention groove 25 and the discs 34 within it causing the gas to be forced into the interior of the insert 30.

The cartridges are configured to meet the stringement operational requirements for such cartridges. It is necessary for the cartridge 10 to have a high surface area to ensure that a large proportion of the mercury in the air or gas sample is trapped or adsorbed. This is met by providing a total surface area for the gold insert 30 of approximately 20 $cm^2$ even though the gold insert 30 has the approximate dimensions of 4 mm diameter and a length of 10 mm. The linear velocity within the cartridges 10 during sampling is quite high, and namely 4 m per second at 3 liters per minute, so that the residence time of sample air within the gold matrix is of the order of 2.5 milliseconds. Accordingly, that air or gas needs to be channelled so as to maximize exposure to the gold surface during this brief residence time.

The insert 30 must provide a low flow restriction, to allow significant volumes of sample air, up to 3 liters per minute, to be easily pumped through in the sampling phase.

A small internal volume is required, to prevent mercury from being diluted or diffused during desorption. This allows cartridges to be rapidly purged from mercury and provides narrow, and repeatable peaks from a detector.

The cartridge 10 should be capable of withstanding hundreds of thousands of heating/cooling cycles without breaking down or loosing adsorption efficiency.

The gold is retained without the use of foreign material such as quartz wool in end plugs or the like. In contrast, all current air sampling cartridges use some form of foreign material. Such foreign material will tend to adsorb water vapour, aromatics and other compounds, which are released during desorption, to give erroneous readings.

In use, during sampling, the adsorption phase of the cycle, the flow is great enough to cause a significant pressure differential between the inlet and outlet of the cartridge. The significant pressure differential occurs when the flow is between one and three liters per minute. This differential presses the insert 30 against the projection 20, ensuring a leak-free seal during sampling. During the desorption phase, the argon carrier gas has a flow rate which is typically 50 to 100 times less than the flow during sampling, so that the pressure differential is not then present. However, the cartridge 10 is designed such that a second phenomenon provides an adequate seal during desorption. The cartridge is heated during desorption, causing the gold insert 10 to expand, this expansion being greater than the expansion of the tube 12. This expansion causes the gold to press firmly against the inner walls of the cartridge, the retaining groove 25 and the orifice seat or projection 20, so as to again provide a leak-tight seal. Argon carrier gas is thus forced to pass along the interior of the insert 30, taking the same path as the sample air. This results in the adsorbed mercury being rapidly and completely desorbed and swept out of the interior of the insert 30 and into the detector (not shown). The identical mesh size of the first 10 discs or screens serves to direct the airflow into the main body of the insert 30, rather than around it. It has been found that the use of identical mesh sizes at the inlet is preferable, although the exact mechanism is not fully understood. It is believed that the identical meshes, even though their weaves are not angularly aligned, have a tendency to create a series of continuous channels extending into the insert, which provide a relatively low flow resistance. In other words, these channels promote flow through the insert, rather than creating a pressure differential promoting flow around the insert where this is possible.

The different mesh sizes in the remainder of the insert 30 encourage flow through it. Additionally, the convoluted path provided by the groove 25 and the projection 20 for any flow attempting to find a boundary path around the insert 30 is convoluted, again forcing it to pass through the insert 30. This maximizes contact between the air or gas and the gold. The alternating disc arrangement also results in the creation of a stronger insert 30 that compresses less during heating and stays in the retaining groove 20, keeping the adsorbent matrix or insert 30 in place at all times.

We claim:

1. A cartridge for collection of a sample of mercury, the cartridge comprising: a housing having an inlet and an outlet and defining a bore for a fluid flow; and an insert comprising a plurality of discrete elements sintered together to form a substantially unitary and porous structure and formed from gold, which insert has a surface area for contact with fluid, that is substantially larger than the surface area of an external profile of the insert, and which insert extends across the bore to cause fluid to flow through the insert, wherein the housing includes a first coupling formation integrally formed with the housing from the material of the housing and the insert includes a second coupling formation integrally formed with the insert from the material of the insert, wherein one of the first and second coupling formations comprises an annular projection and the other one thereof comprises a complementary annular abutment surface, which mechanically engage one another to retain the insert in position for flow in one direction and which are dimensioned to provide a convoluted path substantially to force fluid to pass through the insert.

2. A cartridge as claimed in claim 1, wherein the housing is substantially tubular, and the first coupling formation comprises an internal annular projection, defining an orifice for fluid flow and the second coupling formation is provided by an end face of the insert that engages the annular projection.

3. A cartridge as claimed in claim 2, wherein the housing includes an internal retaining groove, and the metal insert includes a portion projecting into that retaining groove to retain the insert, the retaining groove being provided between the inlet and the annular projection.

4. A cartridge as claimed in claim 2, wherein the metal insert comprises a plurality of wire meshes sintered together and extending generally perpendicularly to the axis of the housing.

5. An insert as claimed in claim 4, wherein the wire meshes comprise first meshes having a first mesh size and second meshes having a second, different mesh size, wherein the first and second meshes alternate with one another within the metal insert.

6. A cartridge as claimed in claim 4, which includes an internal retaining groove located between the inlet and the annular projection, wherein the wire meshes comprise a first group of meshes which are circular and have the same diameter, corresponding to the diameter of the housing, and a second group of meshes which are circular, which are of larger diameter than the first group and which extend into the retaining groove.

7. A cartridge as claimed in claim 6, wherein the wire meshes comprise first meshes having a first mesh size and second meshes having a second, different mesh size, wherein the first and second meshes alternate with one another within the metal insert, wherein the first meshes have a mesh size of 100×100 wires per inch and the second meshes have a mesh size of 52×52 wires per inch.

8. A cartridge as claimed in claim 7, wherein the housing is formed from quartz.

9. A cartridge as claimed in claim 3 or 8, wherein the internal annular projection has a generally conical face on a downstream side and a concave annular face on an upstream side, and defines a circular projection extending generally downstream towards the inlet end engaging the insert.

10. A cartridge, for the collection of a sample of mercury, the cartridge comprising: a housing having an inlet and an outlet and defining a bore for a fluid flow; and an insert comprising a plurality of discrete elements sintered together to form substantially unitary and structure and formed from gold, which insert has a surface area for contact with fluid, that is substantially larger than the surface area of an external profile of the insert, and which insert extends across the bore, wherein the housing includes an internal annular projection formed from material of the housing and defining an orifice for fluid flow and mechanically engaging one end of the insert, to locate the insert and to provide a convoluted path substantially to force fluid to pass through the insert, and at the other end of the insert, the housing includes a retaining groove and the insert includes a portion projecting radially outwardly to engage the retaining groove to provide a further convoluted path to reduce fluid flow around the insert.

11. A cartridge as claimed in claim 10, wherein the internal annular projection has a generally conical face on a downstream side and a concave annular face on an upstream side, and defines a circular projection extending generally downstream towards the inlet end engaging the insert.

12. A cartridge as claimed in claim 10, wherein the insert comprises a plurality of discs which have been sintered together, with each disc comprising a wire mesh formed from at least one of a pure metal, a metal alloy and a metal compound, which is sinterable, and wherein the orientation of the weave of the discs is random.

13. A cartridge as claimed in claim 12, wherein the wire meshes comprise first wire meshes having a first mesh size and second wire meshes having a second, different mesh size, with the first and second meshes alternating with one another within the insert and each wire mesh extending generally transversely across the housing.

14. A cartridge as claimed in claim 10 or 11, which is adapted to collect mercury, wherein in the housing comprises quartz glass and the insert is formed from gold.

* * * * *